(12) United States Patent
Ligny et al.

(10) Patent No.: US 7,988,073 B2
(45) Date of Patent: Aug. 2, 2011

(54) FRAGRANCE DISPENSER

(75) Inventors: Jean-Jacques Ligny, Evreux (FR); Herve Pennaneac'h, Piseux (FR)

(73) Assignee: Valois SAS, Le Neubourg (FR)

( * ) Notice: Subject to any disclaimer, the term of this patent is extended or adjusted under 35 U.S.C. 154(b) by 111 days.

(21) Appl. No.: 12/428,944

(22) Filed: Apr. 23, 2009

(65) Prior Publication Data

US 2009/0266909 A1    Oct. 29, 2009

Related U.S. Application Data

(60) Provisional application No. 61/089,199, filed on Aug. 15, 2008.

(30) Foreign Application Priority Data

Apr. 25, 2008 (FR) ...................... 08 52806

(51) Int. Cl.
  *B65D 1/32* (2006.01)
(52) U.S. Cl. ........ 239/327; 239/601; 239/602; 222/103; 222/215; 222/632; 428/905; 422/123
(58) Field of Classification Search .................. 239/145, 239/326, 327, 601, 602; 222/103, 212, 215, 222/632, 633; 428/905; 422/123
See application file for complete search history.

(56) References Cited

U.S. PATENT DOCUMENTS

| 2,788,921 | A | * | 4/1957 | Galinas | 222/215 |
| 3,897,005 | A | * | 7/1975 | Reiner | 239/327 |
| 4,817,860 | A | | 4/1989 | Shapiro | |
| 5,188,236 | A | | 2/1993 | Sayers et al. | |
| 6,536,635 | B1 | | 3/2003 | Garcia et al. | |
| 6,663,019 | B2 | * | 12/2003 | Garcia et al. | 239/327 |
| 6,997,355 | B2 | * | 2/2006 | Duquet et al. | 222/212 |
| 2003/0094466 | A1 | | 5/2003 | Duquet et al. | |
| 2003/0121939 | A1 | | 7/2003 | Garcia et al. | |
| 2003/0218024 | A1 | | 11/2003 | Garcia et al. | |
| 2004/0000596 | A1 | | 1/2004 | Cuthbert | |
| 2004/0188461 | A1 | | 9/2004 | Pennaneac'h et al. | |

FOREIGN PATENT DOCUMENTS

| FR | 2 791 645 A1 | 10/2000 |
| FR | 2 852 930 A1 | 10/2004 |
| WO | 92/14607 A | 9/1992 |

* cited by examiner

*Primary Examiner* — Steven J Ganey
(74) *Attorney, Agent, or Firm* — Sughrue Mion, PLLC

(57) ABSTRACT

A dispenser for dispensing jets of air laden with fragrance, the dispenser being characterized in that it includes a deformable flexible pouch of variable internal volume containing fragrance microcapsules, the pouch initially being substantially empty of air with the fragrance microcapsules intact, the fragrance microcapsules being broken the first time air enters into the pouch, in such a manner as to load the air in the pouch with fragrance, the pouch including an orifice through which the air penetrates into the pouch, and through which the fragrance-laden air leaves the pouch when the volume of the pouch is varied.

17 Claims, 2 Drawing Sheets

FRAGRANCE DISPENSER

CROSS REFERENCE TO RELATED APPLICATION

This application claims the benefit under 35 U.S.C. §119(e) of pending U.S. provisional patent application Ser. No. 61/089,199, filed Aug. 15, 2008, and priority under 35 U.S.C. §119(a)-(d) of French patent application No. FR-08.52806, filed Apr. 25, 2008.

TECHNICAL FIELD

The present invention relates to a dispenser for dispensing fragrance in spray form, and more particularly in the form of a jet of air laden with fragrance. The advantageous field of application of the present invention is the field of perfumery, but other fields can also be concerned.

BACKGROUND OF THE INVENTION

Dispensers have long been in existence for dispensing fragrance in the form of fine droplets of fluid fragrance. They are called "sprays" and comprise a fluid reservoir on which there is mounted a pump that is actuatable by means of one or more fingers. Actuating the pump causes a dose of fluid to be taken from the inside of the reservoir, puts the dose under pressure, and dispenses said dose in the form of finely-divided droplets. It is also known to dispense the fluid mixed with air. The air is put under pressure so as to form a flow that transports the fine droplets of fragrance.

In addition, samples are already known in the prior art, e.g. fragrance samples in the form of fragrance strips, in which the fragrance is contained in microcapsules that are broken in order to release the fragrance contained therein. In conventional manner, the fragrance microcapsules are in the form of a layer that is applied on a substrate such as a sheet. Another sheet is disposed on the layer of fragrance microcapsules, such that the layer is sandwiched between the two sheets. The user pulls on one of the two sheets in order to detach it from the layer of microcapsules, thereby breaking the microcapsules, and thus releasing their fragrance. That kind of fragrance sample is particularly well suited to being included in the pages of magazines. By way of example, the layer of fragrance microcapsules can be disposed inside a flap formed by a sheet of the magazine. The user thus lifts up the flap, thereby tearing the microcapsules. The fragrance is released into the air in the form of gas or of vapor. The user can inhale or smell the fragrance, particularly on moving closer to the layer of broken microcapsules.

Pump sprays are particularly well suited to dispensing fragrances in the form of liquid droplets. However, they cannot be inserted into a magazine because of the thickness of the spray. In addition, the cost of such sprays is relatively high, particularly for making a free sample. In addition, fragrance strips using microcapsules do not allow targeted dispensing of the fragrance. The fragrance is released in disordered manner as a function of convection currents in the air. The user is practically obliged to stick the nose onto the layer of broken microcapsules, where the smell of the fragrance is mixed with the smell of print and of adhesive. Thus, neither a fine-droplet spray nor a fragrance strip constitutes a fragrance dispenser that is suitable for being used as a sample, particularly a sample for inserting between the pages of a magazine.

BRIEF SUMMARY OF THE INVENTION

An object of the present invention is remedy the above-mentioned drawbacks of prior-art fragrance dispensers by defining a novel dispenser that combines the advantages both of the traditional spray and of the fragrance strip, without reproducing the drawbacks. The dispenser of the invention must be particularly flat or thin so as to be suitable for being inserted between the pages of a magazine. In addition, it should be simple to manufacture and practical to use.

To achieve these objects, the present invention proposes a dispenser for dispensing jets of air laden with fragrance, the dispenser including a deformable flexible pouch of variable internal volume containing fragrance microcapsules, the pouch initially being substantially empty of air with the fragrance microcapsules intact, the fragrance microcapsules being broken the first time air enters into the pouch, in such a manner as to load the air in the pouch with fragrance, the pouch including an orifice through which the air penetrates into the pouch, and through which the fragrance-laden air leaves the pouch when the volume of the pouch is varied. Like a pump spray, the dispenser of the present invention produces a jet, however it differs from the jet of the spray in that it is a jet of air, and not a jet of fine droplets. The air of the jet of the dispenser of the present invention is laden with fragrance in vapor form, and not in liquid form. The dispenser of the present invention thus constitutes a kind of dispenser that is a hybrid between a pump spray and a fragrance strip. Before first use of the dispenser, the pouch contains only intact fragrance microcapsules: it is only on first use that the pouch is inflated by causing the outside air to enter into the pouch for the first time. The deployment of the pouch causes the fragrance microcapsules to break, thereby enabling the air that is contained inside the pouch to become laden with fragrance. Thus, by pressing on the pouch, the fragrance-laden air is expelled from the pouch through the dispenser orifice in the form of a jet of air laden with fragrance.

In a practical embodiment, the pouch includes two walls with the orifice formed in one of them, at least one of the walls being covered at least in part with a layer comprising fragrance microcapsules, the walls being movable relative to each other from an initial state in which they are in contact, the intact microcapsules being substantially not in contact with the air.

The two walls are advantageously connected together via their peripheries. At least one of the walls preferably comprises a flexible sheet. The pouch can be made very simply from a deformable flexible sheet that is folded in half then bonded together at its periphery. The layer of fragrance microcapsules may be applied to one or both of the inside surfaces of the pouch constituted in this way.

According to an advantageous characteristic of the present invention, the dispenser may further include primer means for separating the two walls from each other in such a manner as to break the fragrance microcapsules, and to cause air to penetrate into the pouch. The primer means thus make it possible to initialize the dispenser by breaking the microcapsules and by inflating the pouch with air simultaneously.

Advantageously, the dispenser may further include primer means for separating the two walls from each other in such a manner as to break the fragrance microcapsules, and to cause air to penetrate into the pouch.

In another advantageous aspect of the present invention, the spring means co-operate with primer means that are suitable for causing the spring means to act on the pouch starting from an initial state in which the spring means do not act on the pouch. Thus, in addition to breaking the microcapsules, and to causing air to penetrate into the pouch for the first time, the primer means also enable the spring means to be activated in such a manner as to act on the pouch, by urging it towards its maximum-volume state. The spring means can be used only after the primer means have been put into operation. The spring means make it possible to use the dispenser repeatedly so as to be able to dispense a plurality of jets of fragrance-laden air. The spring means thus fulfill a return function making it possible to return the pouch into its maximum-volume state.

In a practical embodiment, the spring means may comprise a front plate and a rear plate, the pouch being situated between the front and rear plates, the pouch being fastened to the front and rear plates, the primer means comprising spacer means that are selectively moved between an inoperative position in which the two plates extend substantially parallel, corresponding to a minimum-volume state of the pouch, and an operating position in which the plates are spaced apart from each other, at least locally, the front plate being movable relative to the rear plate in such a manner as to flatten the pouch situated between them.

Actuator means may advantageously be provided for positioning the spacer means between the two plates in such a manner as to move them apart, the actuator means comprising a traction member.

The spacer means and the actuator means are advantageously made as a single unit.

The spacer means advantageously comprise a hinged flap that is movable between the inoperative position and the primed position, said flap and the traction member being made as a single unit.

The traction member advantageously forms a fork comprising two branches that are interconnected via a common web.

The pouch is advantageously fastened to a plate between the two branches of the fork.

The spring means are advantageously formed by at least one of: the front plate; the rear plate; and the spacer means.

The orifice advantageously opens out laterally through one of the plates.

The spirit of the present invention is to provide a jet or flow of fragrance in vapor form, and not in the form of finely-divided droplets of liquid. The user can inhale the jet of fragrance-laden air by directing it towards the nose, which is not possible with a jet of finely-divided droplets of liquid. The inventiveness of the present invention mainly relies on the fact that one uses the first ingress of air into the pouch to separate the walls of the pouch and thus break the fragrance microcapsules. So, the user is even not aware that he is breaking the fragrance microcapsules when he is actuating the dispenser in order to enter air inside the pouch.

The advantage of fragrance microcapsules compared to a porous material soaked with liquid fragrance is that there is no risk of leakage through the dispenser orifice that can remain open. In other words, when fragrance microcapsules are used, there is not even any need to provide a closure member for the dispenser orifice. However, for the present invention, it is not excluded to replace the fragrance microcapsules with a porous material soaked with liquid fragrance.

BRIEF DESCRIPTION OF THE DRAWINGS

The invention is described more fully below with reference to the accompanying drawings which show an embodiment of a dispenser of the invention by way of non-limiting example.

In the figures.

DETAILED DESCRIPTION OF THE INVENTION

The dispenser of the present invention for dispensing jets of fragrance-laden air comprises a deformable flexible pouch 3 that is advantageously associated with spring means and primer means that are used to initialize the pouch and to cause its internal volume to vary, as described below. The spring means and primer means surround the pouch like a case.

Figure 1:
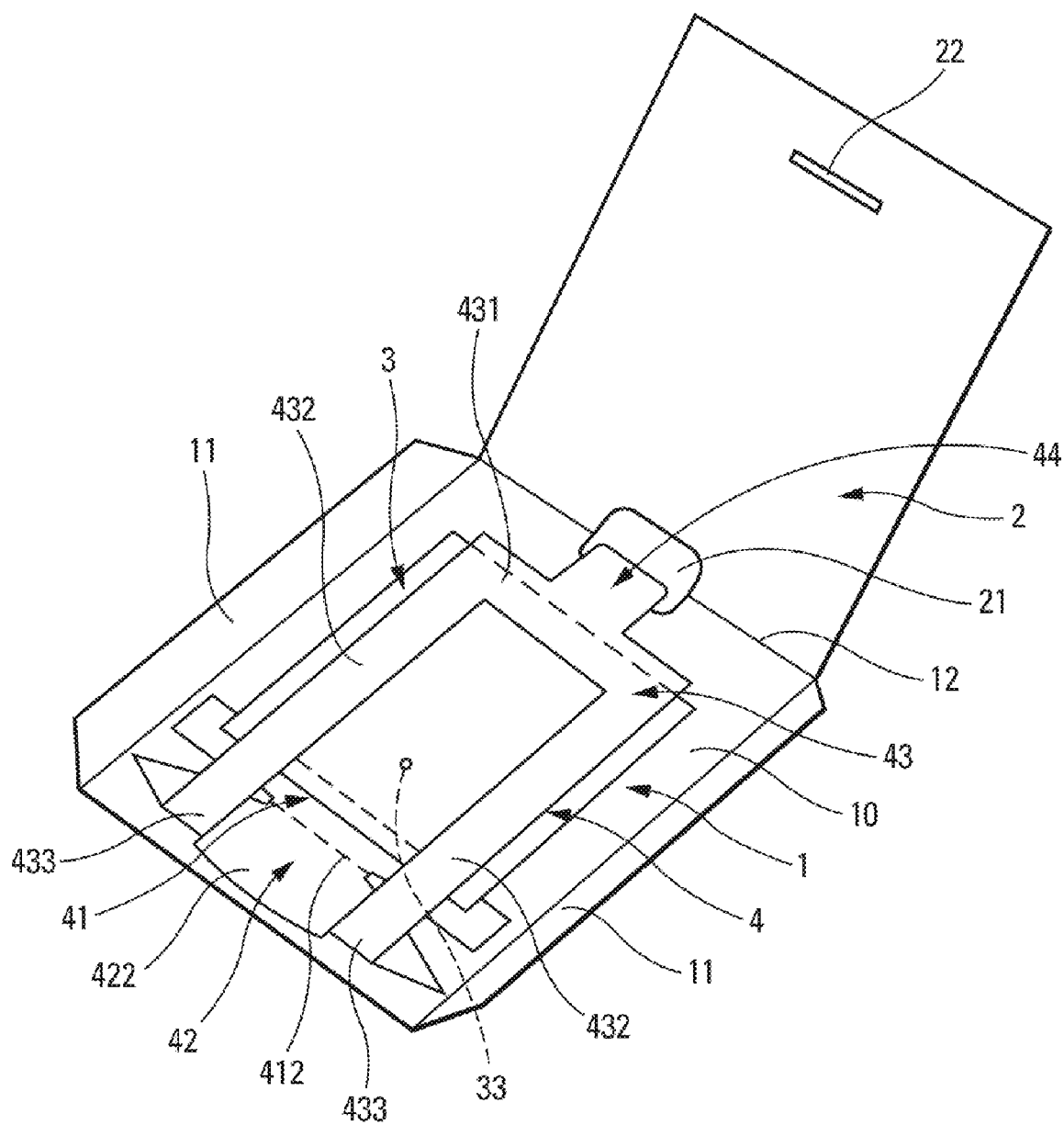
FIG. 1 is a perspective view as seen from above of a dispenser of the invention in its unfinished state in order to show its internal structure.

The deformable flexible pouch 3 comprises two walls 31, one of which has a dispenser orifice 33 formed therein. In FIG. 1, the lead line to the orifice 33 is drawn as a dashed line to indicate that the orifice is situated on the bottom face of the pouch that is not visible in FIG. 1. By way of example, the two walls 31 of the pouch can be made from a flexible sheet that is folded in half and bonded together at its periphery. It is also possible to make the pouch from two separate flexible sheets. It is also possible to make the pouch with a flexible sheet and a rigid or semi-rigid wall. It can also be envisaged to use two rigid walls that are interconnected via a flexible element e.g. in the form of a bellows. When the pouch uses one or more flexible sheets, said sheets can be made from a laminate of aluminum and of plastics material. The sheets can be bonded together by merely heat-sealing the plastics material.

Figure 2:
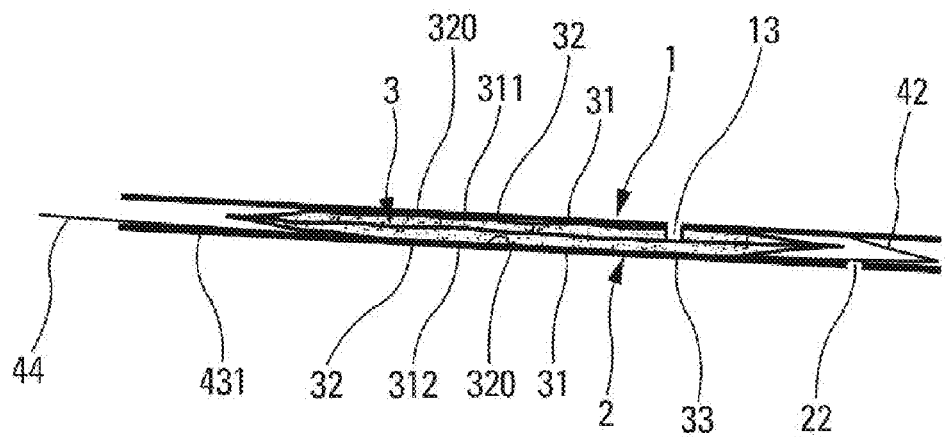
FIGS. 2, 3, and 4 are vertical-section views through the FIG. 1 dispenser.
Figure 3:
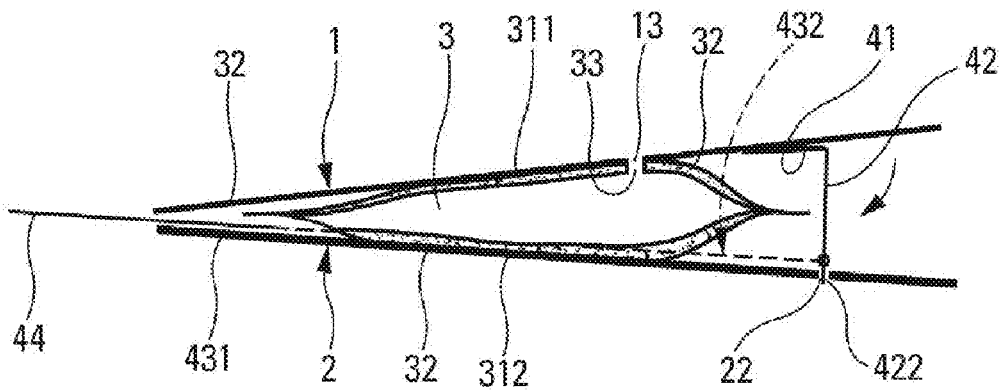
Figure 4:
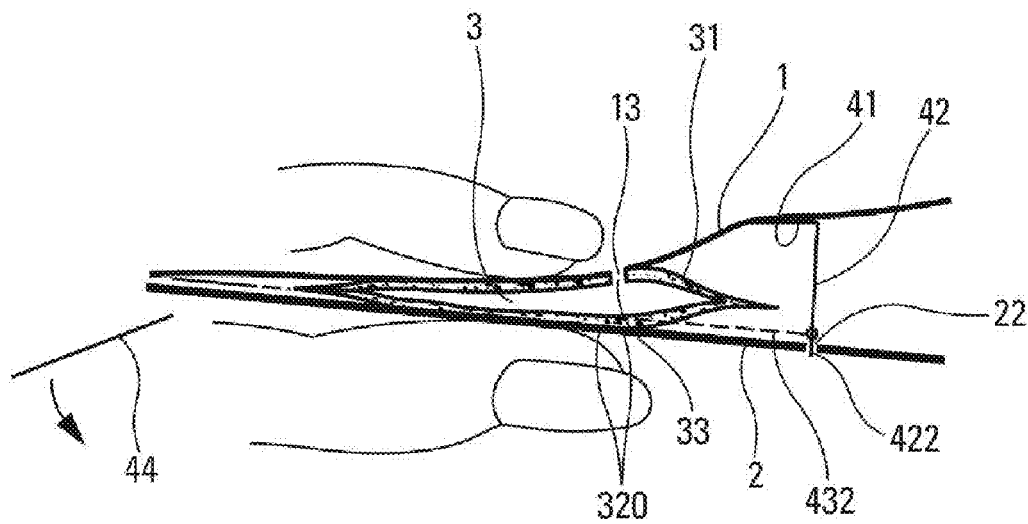

In the invention, the deformable flexible pouch 3 contains fragrance microcapsules 320, e.g. in the form of one or two layers 32 of fragrance microcapsules 320 applied to one or both walls 31 of the pouch. In FIGS. 2 to 4, it should be observed that the pouch contains two adjacent layers 32 of fragrance microcapsules 320, respectively applied to each of the walls 31 of the pouch. The thickness of the layers 32 is deliberately exaggerated in order to make them visible in the figures. In reality, the layers are extremely thin and imperceptible in section views. Similarly, the microcapsules 320 are shown in the layers 32, but this does not reflect reality. In the initial state, as shown in FIGS. 1 and 2, the two layers 32 of fragrance microcapsules 320 are adjacent and bonded together. In this initial state, the pouch contains only a small amount of air, if any. However, the dispenser orifice 33 can remain open given that there is no risk of leakage as a result of using fragrance microcapsules. In addition, there is also no risk of air penetrating into the pouch, given that the two layers 32 are bonded together. The same applies when the pouch 3 contains only a single layer 32 of fragrance microcapsules: the layer 32 would thus be disposed between the two walls 31 of the pouch. The pouch thus presents thickness of millimeter order.

In the ambit of the invention, it is also possible to use a fragrance-soaked porous material instead of fragrance microcapsules. However, the soaked porous material presents the disadvantage of potentially leaking when it is subjected to stress, as occurs when the dispenser is disposed between the pages of a magazine. For other uses in which the dispenser is not subjected to stress, it can be envisaged to replace the microcapsules with a soaked porous material.

In order to release their content, fragrance microcapsules need to be broken. It is well known in the prior art to break such microcapsules by detaching them from, or by pulling them off, a sheet, as with fragrance strips. For the deformable and flexible pouch 3 of the invention, it is therefore necessary to separate or to detach the two layers 32 from each other. This operation could be performed manually by pulling directly on the walls 31 of the pouch. By way of example, a pull tab could be provided on each of the walls 31, such that the user could pull on the walls 31 by pulling on the pull tabs. The present invention proposes another technique for separating the layers from each other, and for producing the jet of fragrance-laden air. To do this, the present invention proposes primer means and spring means that make it possible firstly to separate the layers 32 from each other, and secondly to actuate the pouch so as to emit jets of fragrance-laden air.

In this embodiment, the spring means and the primer means are in the form of a top plate 2 and a bottom 1 that are associated with a pivot flap 42 and with a traction member 43, 44 so as to cause the flap to pivot. The flap 42 fulfils a priming function making it possible to activate the spring means. It could also provide a spring function. At least one of the two plates is elastically deformable, in such a manner as to perform a spring function if the flap does not already perform it. Preferably, both plates are elastically deformable and the flap is rigid. Both of the plates 1 and 2 can be made by folding a single plate in half via a connection fold 12, as in the figures. A cutout or notch 21 is formed at the connection fold 12. The notch can be made by a window that extends on either side of the fold, and that is then folded in half.

The plate 1 is formed by a panel 10 and by two side borders 11 that can be folded onto the panel. The plate 1 is provided with a hole 13. The plate 2 is connected to the panel 10 via the fold 12. The plate 2 is substantially the same size as the panel 10, such that they can be superposed.

A fastener stub 41 is advantageously bonded on the panel 10. The stub can also be made integrally with the plate 1. The flap 42 can be hinged relative to the stub 41 by pivoting about a line 412. The flap serves as primer means in the form of spacer means, as described below. The flap is further provided with a small blocking tab 422 having a function that is described below. The stub and the flap can be made as a single piece. The flap is advantageously situated in the proximity of the edge that is opposite from the fold 12.

The plate 2 is formed with a slot 22 for receiving the blocking tab 422 of the plate 1.

The plates are for fastening together, advantageously for heat-sealing together at the borders 11. A kind of envelope is thus obtained that is sealed on three sides, and that is open on the side on which the hinged flap 42 is formed. The deformable pouch 3 is disposed between the two plates, inside the envelope they form. The dispenser orifice 33 is advantageously positioned at the hole 13. The pouch 3 can advantageously be fastened inside the envelope that is constituted by the two plates. By way of example, the pouch can be fastened in two zones 311 and 312 to each of the plates.

When the flap 42 extends in the same plane as the remainder of the plate 1, as shown in FIGS. 1 and 2, the plate 2 extends substantially parallel to the plate 1, with the deformable pouch 3 interposed between them. The deformable pouch 3 advantageously contains only the layer(s) 32 of fragrance microcapsules that are still intact, such that it presents a configuration that is particularly flat. Thus, when disposed between the two plates 1 and 2, it creates a small amount only of additional thickness, and the two plates thus appear to be superposed with almost nothing between them. This is shown in FIG. 2 in which the thickness of the two layers 32 of fragrance microcapsules has been exaggerated in order to make them visible. The real total thickness of the dispenser can be in the range about 2 mm to 3 mm. In its rest state, the dispenser is thus suitable for transporting and for storing. The deformable pouch 3 that forms the actuator walls is not subjected to any stress. In addition, the plates 1 and 2 are not subjected to any stress.

In order to prime the dispenser, it suffices to cause the flap 42 to pivot about the hinge line 412, towards the plate 2, as shown by the small arrow in FIG. 3. The fold line 412 is advantageously curved, e.g. in the shape of a circular arc. In symmetrical manner, the edge of the flap where the tab is formed can also be curved. Thus, when the flap 42 pivots towards the plate 2, each of the plates takes on curvature that corresponds respectively to the fold line and to the free edge. The flap is hinged by pivoting until its free edge comes to bear against the plate 2, and its small blocking tab 422 comes to be housed inside the slot 22 formed in the plate 2. This is shown in FIG. 3. The flap thus extends substantially perpendicularly both to the plate 1 and to the plate 2. As a result of the tab 422 being engaged in the slot 22, the flap is blocked in position. By way of example, the flap can be made in rigid manner. It thus constitutes spacer means that make it possible to hold the two plates apart from each other.

Given that the pouch 3 is fastened to the plate 1 at 311 and to the plate 2 at 312, moving apart the two plates as a result of interposing the spacer flap also has the effect of moving apart the walls of the pouch. The two layers 32 of fragrance microcapsules are thus detached or torn apart from each other, thereby causing the fragrance microcapsules to break, thereby releasing their fragrance content. The increase in the internal volume of the pouch is accompanied by air being drawn in through the dispenser orifice 33 for the first time. It is possible to move the plates apart only if air can penetrate into the reservoir. In the invention, the plates are made of an elastically-deformable material that imparts a resilient return characteristic thereto. Thus, once the dispenser is in the configuration shown in FIG. 3, it can be actuated by pressing on the plate 1 by means of a finger and by holding the other plate by means of the thumb. This is shown in FIG. 4. Each of the plates can form return-spring means. In the embodiment in the figures, only the plate 1 forms resilient return means, while the plate 2 can be completely rigid and can serve as a reaction surface. It is also possible to imagine that only the flap is elastically deformable, and that both plates are rigid. A flexible flap with a deformable plate can also be envisaged.

The plates can move towards each other by deforming the pouch. This causes the air in the pouch 3 to be put under pressure, thereby causing the fragrance-laden air to be expelled in the form of a jet.

It should thus be observed that the spacer flap 42 forms primer means making it possible to bring the plates into a spaced-apart configuration.

The spring means and the primer means are in the form of an envelope that surrounds the pouch 3. It is also possible to imagine embodiments in which the spring means and primer means are in the form of two narrow strips or blades, one of which comprises a priming spacer flap. The flexible pouch 3 would thus be disposed between the two strips.

In the invention, the fluid dispenser is provided with actuator means that are designated overall by the numerical reference 4 in FIG. 1. The actuator means can include in their definition, the flap 42 and the fastener stub 41, given that they can be made integrally with the remainder of the actuator means 4. The actuator means 4 comprise a traction member 43, 44 that extends between the flap 42 and the notch 21. The traction member is advantageously connected integrally with the edge of the flap 42 where the blocking tab 422 is formed. In addition, the traction member includes a pull tab 44 that is initially positioning in the notch 21. By pulling on the pull tab 44, the traction member transmits the traction force to the flap 42 that is caused to pivot from its inoperative position shown in FIG. 2 into its primed position shown in FIG. 3. The final position is the position in which the blocking tab 422 becomes housed in the slot 22 of the plate 2. The user should immediately understand that it is necessary to grip the pull tab 44 and pull thereon. The traction member extends between the two plates 1 and 2.

This is the general concept provided for the actuator means of the invention.

However, the figures illustrating the present invention provide a very practical embodiment for the actuator means 4. More particularly with reference to FIG. 1, it can be seen that the actuator means 4 form the traction member that comprises a force transmission fork 43 and a pull tab 44. The fork and the pull tab can be made as a single piece, or, in a variant, the pull tab 44 can be fastened, e.g. by adhesive, to the fork 43. The fork 43 comprises two side branches 432 that are substantially parallel, and that are connected at one of their ends to a common web 431. The branches 432 extend substantially parallel to the borders 11 of the plate 1. The web 431 is situated in the proximity of the notch 21. The branches 432 define connection ends 433 that are connected to the flap 42 on either side of the blocking tab 422. The fork 43 and the flap 42 can be made as a single piece, advantageously with the fastener stub 41. The pull tab 44 is connected to the fork 43 at the common web 431. Initially, before first use, the flap 42 is pressed against the plate 1. The pull tab 44 is thus positioned in the groove 21 without projecting out therefrom. The user can grip the pull tab 44 and pull thereon in such a manner as to cause the flap 42 to pivot. By continuing to pull, the user detaches the pull tab 44 from the fork 43. This is shown in FIG. 4.

The deformable pouch 3 is disposed between the fork 43 and the plate 1, as can be seen in FIG. 1, the pouch 3 being shown by dashed lines. The fork shape firstly enables traction forces to be distributed better over the flap 42, and also enables the pouch 3 that is situated between the two branches to be fastened in centered manner on the zone 312. The fork shape also makes it possible to reach abutting contact between the common web 431 and the fold 12 at the end of traction, thereby resulting in the pull tab 44 being detached from the fork 43.

The invention claimed is:

1. A dispenser for dispensing jets of air laden with fragrance, the dispenser being characterized in that it includes a deformable flexible pouch of variable internal volume containing fragrance microcapsules, the pouch initially being substantially empty of air with the fragrance microcapsules intact, the fragrance microcapsules being broken the first time air enters into the pouch, in such a manner as to load the air in the pouch with fragrance, the pouch including an orifice through which the air penetrates into the pouch, and through which the fragrance-laden air leaves the pouch when the volume of the pouch is varied.

2. A dispenser according to claim 1, in which the pouch includes two walls with the orifice formed in one of them, at least one of the walls being covered at least in part with a layer comprising the fragrance microcapsules, the walls being movable relative to each other from an initial state in which they are in contact, the intact fragrance microcapsules being substantially not in contact with the air.

3. A dispenser according to claim 2, in which the two walls are connected together via their peripheries.

4. A dispenser according to claim 2, in which at least one of the walls comprises a flexible sheet.

5. A dispenser according to claim 2, further including primer means for separating the two walls from each other in such a manner as to break the fragrance microcapsules, and to cause air to penetrate into the pouch for the first time.

6. A dispenser according to claim 5, further including spring means for urging the pouch into a maximum-volume state, the pouch being flattenable against the action of the spring means so as to expel the fragrance-laden air out from the pouch.

7. A dispenser according to claim 6, in which the spring means co-operate with the primer means for causing the spring means to act on the pouch starting from an initial state in which the spring means do not act on the pouch.

8. A dispenser according to claim 7, in which the spring means comprise a front plate and a rear plate, the pouch being situated between the front and rear plates, the pouch being fastened to the front and rear plates, the primer means comprising spacer means that are selectively moved between an inoperative position in which the two plates extend substantially parallel, corresponding to a minimum-volume state of the pouch, and an operating position in which the plates are spaced apart from each other, at least locally, the front plate being movable relative to the rear plate in such a manner as to flatten the pouch situated between them.

9. A dispenser according to claim 8, in which actuator means are provided for positioning the spacer means between the two plates in such a manner as to move them apart, the actuator means comprising a traction member.

10. A dispenser according to claim 9, in which the spacer means and the actuator means are made as a single unit.

11. A dispenser according to claim 10, in which the spacer means comprise a hinged flap that is movable between the inoperative position and the primed position, said flap and the traction member being made as a single unit.

12. A dispenser according to claim 9, in which the traction member forms a fork comprising two branches that are interconnected via a common web.

13. A dispenser according to claim 12, in which the pouch is fastened to a plate between the two branches of the fork.

14. A dispenser according to claim 8, in which the spring means are formed by at least one of: the front plate; the rear plate; and the spacer means.

15. A dispenser according to claim 8, in which the orifice opens out laterally through one of the plates.

16. A dispenser for dispensing jets of air laden with fragrance, the dispenser comprising:
    a deformable flexible pouch of variable internal volume and having an orifice;
    fragrance microcapsules contained in said pouch;
    wherein, in an initial state, the pouch is substantially empty of air with the fragrance microcapsules intact, the fragrance microcapsules being broken the first time air enters into the pouch through said orifice, so as to cause the air in the pouch to be laden with fragrance, and the fragrance-laden air being dispensed from the orifice in a form of vapor when the volume of the pouch is varied.

17. The dispenser according to claim 16, wherein the pouch comprises two walls joined along peripheries thereof, with said orifice formed in one of said two walls, at least one of said two walls having an inner surface formed with a layer comprising the fragrance microcapsules, said two walls being movable relative to each other, from the initial state in which said two walls are in contact and the intact fragrance microcapsules are substantially not in contact with air, to a subsequent state in which said two walls are separated from each other except along their peripheries so that the pouch is filled with air that has entered through said orifice and the fragrance microcapsules are broken.

\* \* \* \* \*